(12) United States Patent
Panzera et al.

(10) Patent No.: US 6,206,958 B1
(45) Date of Patent: *Mar. 27, 2001

(54) DENTAL PORCELAIN COMPOSITIONS

(75) Inventors: Paul Panzera, Mt. Holly; Jana N. Pruden, Bellemead; Dmitri Brodkin, West Orange; Lisa M. Kaiser, Parsippany; Richard A. Brightly, Monmouth Junction; Carlino Panzera, Bellemead, all of NJ (US)

(73) Assignee: Jeneric/Pentron, Incorporated, Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/354,082

(22) Filed: Jul. 15, 1999

Related U.S. Application Data

(63) Continuation-in-part of application No. 09/118,539, filed on Jul. 17, 1998, now Pat. No. 6,022,819.

(51) Int. Cl.[7] .................................................... C03C 8/16
(52) U.S. Cl. .................. 106/35; 433/202.1; 433/206; 433/212.1; 427/3.26; 427/2.27; 427/2.29; 501/16; 501/17; 501/20; 501/21; 501/24; 501/25; 501/26; 501/59; 501/57; 501/63; 501/64; 501/66; 501/68; 501/69; 501/70; 501/72

(58) Field of Search .................. 501/20, 16, 17, 501/21, 24, 25, 26, 59, 57, 63, 64, 66, 67, 68, 69, 70, 72; 106/35; 433/202.1, 206, 212.1; 427/2.29, 2.26, 2.27

(56) References Cited

U.S. PATENT DOCUMENTS

| | | | |
|---|---|---|---|
| 4,557,691 | 12/1985 | Martin et al. | 433/199.1 |
| 4,806,383 | 2/1989 | Poltz | 427/2 |
| 5,679,144 | 10/1997 | Thiel et al. | 501/70 |
| 6,022,819 | * 2/2000 | Panzera et al. | 510/20 |

* cited by examiner

*Primary Examiner*—C. Melissa Koslow
(74) *Attorney, Agent, or Firm*—Ann M. Knab

(57) ABSTRACT

Porcelain compositions of the present invention comprises particulate of one or more glass or glass-ceramic powder components. Additionally, one or more opacifing agents, pigments, fluorescing agents and the like may be included in the composition. Based on volume percent, the particulate has a $d_{10}$ of from about 1.1 and about 1.8 microns; a $d_{50}$ of from about 3 to about 6 microns; a $d_{90}$ of from about 8 to about 16 microns; and about 1.0 to about 4.0% by volume of the particulate has a particle size greater than or equal to about 20 microns. The mean particle size is preferably in the range of about 3.0 microns to about 7.5 microns.

52 Claims, No Drawings

DENTAL PORCELAIN COMPOSITIONS

CROSS-REFERENCE TO RELATED APPLICATIONS

This is a continuation-inpart application to application number 09/118,539 filed Jul. 17, 1998 entitled DENTAL PORCELAIN COMPOSITIONS, now U.S. Pat. No. 6,022,819.

TECHNICAL FIELD

The present invention relates generally to porcelain compositions and more specifically to dental porcelain powder compositions for use as an initial layer on top of an alloy coping or ceramic core material in the preparation of dental restorations.

BACKGROUND OF THE INVENTION

Dental restorations, such as crowns, bridges and the like, are typically made of a metallic or porcelain core framework with one or more porcelain layers coated thereon. The porcelain layers provide strength, wear resistance and favorable aesthetics to the dental restorations. In porcelain fused-to-metal (PFM) restorations, it is important that the firing temperature of the porcelain be at least 100° C. below the solidus temperature of the alloy used as the metal framework and that the coefficient of thermal expansion of the porcelain (in the range of room temperature to 450° C.) be only very slightly less than that of the metal so that no stress cracks are produced in the porcelain layer during firing and cooling down. Ceramic cores are advantageous in the fabrication of dental restorations because concerns regarding effective concealment of the metal color do not exist. Similar to metal cores, when a ceramic core is used, any porcelain applied to the ceramic framework must possess a coefficient of thermal expansion that is slightly less than that of the ceramic to prevent failure in the porcelain due to stresses caused by thermal expansion mismatch.

U.S. Pat. No. 5,679,144 is directed to a powder composition comprising one or more feldspar frits and $CeO_2$ as an opacifier. The frits have a particle size distribution of $d_{50}$ of 3 to 6 microns, $d_{90}$ of 12 to 16 microns and a maximum grain size of less than 20 microns. As set forth therein, since the paste may segregate, it is supplied in ajar or box so that it can be stirred up before use if necessary. Also, due to the relatively fine particle size, pinholes or steam tearing may occur in the final restoration if moisture is not allowed to evaporate freely.

U.S. Pat. No. 4,557,691 is directed to a porcelain paste comprising a porcelain powder mixed with an aqueous colloidal dispersion of a urethane polymer. The product is sold in a syringe and may dry out in the syringe before use due to evaporation of ammonia and water.

U.S. Pat. No. 4,806,383 is directed to a method of applying opaque dental ceramic material to a metal structure that requires an additional step of dusting a ceramic powder having an average grain size of from 40 microns to 100 microns onto the applied opaque paste, firing the material, and applying additional ceramic and firing same. The large particle size affects the handling characteristics of the paste and also results in significant settling of the powder in the liquid. In addition, the dusting step requires additional time and skill to make the restoration.

There is a need to prevent settling of the powder from the liquid component in porcelain paste compositions so that the paste composition can be provided in a variety of packaging forms including syringes. It is desirable to produce a dental porcelain paste that can be applied easily in thin coats. It is advantageous that sufficient coverage of the core framework is achieved without the need for dusting of additional porcelain powder thereon.

SUMMARY OF THE INVENTION

These and other objects and advantages are accomplished by the porcelain compositions of the present invention comprising one or more glass or glass-ceramic powder components. Additionally, one or more opacifying agents, pigments, fluorescing agents and the like may be included in the composition. The amount of opacifier can be varied to create porcelains with varying opacity which can be used for different applications. The amount and type of pigments can be varied to create different shades of dental porcelain. The porcelain compositions may vary depending upon the specific thermal properties desired. The fusion temperature of the porcelain compositions is in the range of from about 750° to about 1010° C. and the coefficient of thermal expansion is in the range of from about 2 to about $18 \times 10^{-6}/°$ C. and more preferably in the range of from about 3 to about $16 \times 10^{-6}/°$ C. (measured from room temperature to 450° C.). The compositions are also characterized by the particle size of the particulate as defined by $d_{10}$, wherein ten percent of the volume of particles is smaller than the indicated size; $d_{50}$, wherein fifty percent of the volume of particles is smaller than the indicated size and $d_{90}$ wherein ninety percent of the volume of particles is smaller than the indicated size. For example, a $d_{10}$ equal to 1.1 microns indicates that ten percent of the volume of particles is smaller than 1.1 microns.

In one embodiment of the present invention, the porcelain has a $d_{50}$ of from about 3 to about 6 microns, and a $d_{90}$ of from about 8 to about 16 microns, and the maximum particle size of the particulate is greater than or equal to about 20 microns. Preferably, the porcelain further has a $d_{10}$ of from about 1.1 microns to about 1.8 microns. Preferably the maximum particle size is no greater than about 60 microns. Preferably, about 1.0% to 4% of the particulate is greater than about 20 microns and more preferably, about 1.5% to about 3.5% of the particulate has a particle size greater than about 20 microns. The mean diameter of the volume distribution (hereinafter referred to as the "mean particle size") is preferably in the range of from about 3.0 microns to about 7.5 microns.

More preferably, the porcelain has a $d_{50}$ of from about 3.5 to about 5.5 microns, and a $d_{90}$ of from about 10 to about 14.5 microns, and the maximum particle size of the particulate is greater than or equal to about 20 microns. More preferably, the porcelain further has a $d_{10}$ of from about 1.15 microns to about 1.65 microns. More preferably, the maximum particle size is no greater than about 50 microns. The mean particle size is more preferably in the range of about 3.5 microns to about 6.75 microns.

In a preferred embodiment of the method of the present invention, two or more glass and/or glass-ceramic flits are milled separately. The milled flits are then mixed together resulting in a mixture having particle sizes in the desired particle range in accordance with the invention herein. Opacifiers, pigments and the like may also be added to the mixture. The mixture is then ready for application to a core material.

In another embodiment of the method of the present invention, two or more glass and/or glass-ceramic flits are mixed together. The mixture is then milled to the desired particle sizes and an opacifying agent, pigments and the like may then be added to the mixture. The average particle size of the opacifier typically ranges from about 0.2 to about 2.8 microns. The mixture is then ready for application to a core material.

In another embodiment of the method of the present invention, various oxides or precursors thereof are mixed together and melted to prepare a porcelain frit. Suitable precursors include silica, alumina, boric acid, feldspar, calcium carbonate, sodium carbonate, potassium carbonate, magnesium carbonate, lithium carbonate, and/or barium compounds. The frit is then milled to the desired particle sizes and an opacifying agent, pigments and the like may then be added to the porcelain frit to obtain an opaque porcelain frit. The mixture is then ready for application to a core material.

In yet another embodiment of the method of the present invention, one or more glass and/or glass-ceramic frit compositions are milled separately to the desired particle size. The frits are then mixed together and the mixture may be combined with an opacifying agent, pigments and the like. The mixture is then ready for application to a core material.

In still another embodiment of the method of the present invention, one or more glass and/or glass ceramic frits are milled separately. The frits are then mixed and an opacifying agent may be added thereto. The mixture is then milled to the desired particle sizes. The mixture is then ready for application to a core material. Optionally, pigments or other additives may be added to the mixture.

The porcelains in accordance with the present invention are especially suitable for use in dental restorations as an initial layer on top of an alloy coping such as Rexillium® III alloy available from Jeneric/Pentron Inc., Wallingford, Conn. or ceramic core material such as the Optimal Pressable Ceramic® system also available from Jeneric/Pentron Inc. Additional porcelains may then be added on top of the opaque layer to create an esthetic restoration. The porcelains herein may also be used as inlays, onlays and veneers in the manufacture of dental restorations.

DETAILED DESCRIPTION OF THE INVENTION

The present invention is directed to a dental porcelain comprising one or more glass or glass-ceramic powders. Additives such as opacifying agents, pigments, fluorescing agents and the like may be included in the composition. Based on volume percent, the particle size of the porcelain powder is distributed having a $d_{50}$ from about 3 to about 6 microns, and a $d_{90}$ from about 8 and about 16 microns, and the maximum particle size of the particulate is greater than or equal to about 20 microns. Preferably, the powder further has a $d_{10}$ of from about 1.1 microns to about 1.8 microns. Preferably the maximum particle size is no greater than about 60 microns. Preferably, about 1.0% to 4% of the particulate is greater than about 20 microns and more preferably, about 1.5% to about 3.5% of the particulate has a particle size greater than about 20 microns. The mean particle size is preferably in the range of about 3.0 microns to about 7.5 microns.

More preferably, the porcelain has a $d_{50}$ of from about 3.5 to about 5.5 microns, and a $d_{90}$ of from about 10 to about 14.5 microns, and the maximum particle size of the particulate is greater than or equal to about 20 microns. More preferably, the porcelain further has a $d_{10}$ of from about 1.15 microns to about 1.65 microns. Preferably, the maximum particle size is no greater than about 50 microns. The mean particle size of the particles is more preferably in the range of about 3.5 microns to about 6.75 microns.

The particle size distribution of the porcelain powder provides a porcelain having good forming and processing properties that will resist separation of the powder from the liquid. The porcelain is easily applied and spread on the core framework in thin layers. The thin layers provide proper coverage of the core framework. The combination of ultrafine particles, i.e., less than about 14 to about 16 microns, with coarse particles, i.e., greater than about 20 microns, and preferably in the range of from about 20 to about 60 microns, provides a product having good handling and drying properties. The ultrafine particles aid in preventing settling and promote good handling characteristics and the coarse particles allow for the escape of steam during drying thereby preventing tears and pinholes in the final product. The amount of coarse particles is limited to the extent that settling out of particles is reduced or prevented.

Table 1 below lists examples pertaining to particle size representative of the present invention.

TABLE 1

| powder | 1 | 2 | 3 | 4 | 5 | 6 | 7 | 8 |
|---|---|---|---|---|---|---|---|---|
| mean particle size of powder | 3.89 | 5.37 | 5.94 | 4.72 | 5.83 | 5.09 | 6.71 | 7.14 |
| $d_{10}$ | 1.15 | 1.31 | 1.37 | 1.24 | 1.33 | 1.31 | 1.62 | 1.61 |
| $d_{50}$ | 2.91 | 3.73 | 4.08 | 3.49 | 4.06 | 3.66 | 5.10 | 5.30 |
| $d_{90}$ | 8.00 | 11.27 | 12.88 | 9.81 | 13.07 | 10.58 | 14.28 | 15.52 |
| maximum particle size | 20 | 50 | 50 | 35 | 35 | 50 | 35 | 40 |
| percentage of particles > 20 microns | 0 | 2.50 | 3.50 | 1.50 | 2.5 | 2.0 | 3.5 | 4 |

The fusion temperature of the porcelain compositions is in the range of from about 750° C. to about 1010° C. and the coefficient of thermal expansion is in the range of from about 2 to about $18 \times 10^{-6}/°$ C. and more preferably in the range of from about 3 to about $16 \times 10^{-6}/°$ C.

Preferably the main components of the composition are present in the following ranges in weight percent:

from about 40% to about 85% $SiO_2$ from about 2% to about 18% $Al_2O_3$ from about 2% to about 23% flux from about 0 to about 6% MeO from about 0 to about 25% opacifier from about 0 to about 30% pigment whereby the flux includes but is not limited to one or more of $K_2O$, $Na_2O$, $Li_2O$, CaO, $P_2O_5$, F, BaO, and $B_2O_3$; Me includes one or more metals compounds including but not limited to Zn and Mg; the opacifier includes but is not limited to one or more of $TiO_2$, $ZrO_2$, $CeO_2$, $Y_2O_3$, $ZrO_2.SiO_2$; and SnO2; and the pigment includes one or more conventional pigmenting agents commonly used in dental porcelains such as vanadates, manganates, chromates, other transition metal oxides and the like.

Examples of preferred porcelain compositions are summarized in Table 2 below.

TABLE 2

| % by weight | 1 | 2 | 3 | 4 | 5 | 6 | 7 | 8 | 9 | 10 | 11 |
|---|---|---|---|---|---|---|---|---|---|---|---|
| $SiO_2$ | 54.87 | 53.99 | 50.67 | 54.86 | 57.80 | 54.40 | 53.54 | 82.40 | 51.35 | 45.93 | 43.08 |
| $Al_2O_3$ | 7.29 | 13.49 | 13.34 | 10.45 | 17.55 | 2.40 | 8.13 | 2.00 | 14.00 | 13.19 | 12.36 |
| ZnO | — | 0.02 | 0.05 | — | — | — | — | — | 0.04 | 0.03 | 0.03 |
| CaO | 2.60 | 0.85 | 0.62 | 1.91 | 4.25 | 4.00 | 0.99 | — | 0.70 | 0.66 | 0.62 |
| MgO | 1.81 | 0.14 | 0.18 | 1.20 | 3.40 | 3.20 | 0.73 | — | 0.16 | 0.17 | 0.16 |
| $Li_2O$ | 0.64 | 1.18 | 1.09 | 1.02 | — | — | 0.58 | — | 1.13 | 1.03 | 0.96 |
| $K_2O$ | 5.56 | 10.15 | 10.43 | 7.68 | 0.85 | 0.80 | 11.01 | — | 9.46 | 8.49 | 7.96 |
| $Na_2O$ | 8.06 | 2.76 | 2.39 | 5.46 | 12.75 | 12.00 | 6.49 | 3.60 | 2.73 | 2.43 | 2.28 |
| $TiO_2$ | — | — | 0.70 | 4.00 | — | — | — | — | — | — | — |
| $CeO_2$ | 0.13 | 0.29 | 0.33 | 0.22 | — | — | 0.06 | — | 0.31 | 0.27 | 0.25 |
| $SnO_2$ | — | 17.00 | 20.20 | 12.00 | — | — | — | — | — | — | — |
| $ZrO_2$ | 17.00 | — | — | — | — | 20.00 | 17.00 | — | 20.00 | 14.80 | 13.90 |
| F | 0.15 | — | — | — | — | — | 1.33 | — | — | — | — |
| BaO | 0.88 | 0.06 | — | 0.60 | 1.70 | 1.60 | — | — | 0.06 | 0.07 | 0.07 |
| $B_2O_3$ | 1.02 | 0.06 | — | 0.60 | 1.70 | 1.60 | 0.14 | 12.0 | 0.06 | 0.07 | 0.07 |
| Pigment | — | — | — | — | — | — | — | — | — | 12.86 | 18.26 |

The porcelain compositions prepared in accordance with the present invention are preferably used in dental restorations as an initial layer on top of an alloy coping or ceramic core material. Additional porcelains may then be added on top of the opaque layer to create an esthetic restoration.

In a preferred embodiment of the method of the present invention, two or more glass and/or glass-ceramic flits are milled separately. The milled frits are then mixed together resulting in a mixture having particle sizes in the desired particle range in accordance with the invention herein as set forth herein. Opacifiers, pigments and the like may also added to the mixture. The mixture is then ready for application to a core material.

In another embodiment of the method of the present invention, two or more glass and/or glass-ceramic frits are mixed together. The mixture is then milled to the desired particle size and an opacifying agent such as $TiO_2$, $Y_2O_3$, $SnO_2$, $ZrO_2$, $CeO_2$, and/or $ZrO_2 \cdot SiO_2$, pigments, and the like may then added to the mixture.

In another embodiment of the method of the present invention, various oxides or precursors thereof are mixed together and melted to prepare a porcelain frit. Suitable precursors include silica, alumina, boric acid, feldspar, calcium carbonate, sodium carbonate, potassium carbonate, magnesium carbonate, lithium carbonate, and/or barium compounds. The frit is then milled to the desired particle sizes and an opacifying agent, pigments, and the like may then added to the porcelain frit.

In yet another embodiment of the method of the present invention, one or more glass and/or glass-ceramic frit compositions are milled separately to the desired particle size. The frits are then mixed together and the mixture may then be combined with an opacifying agent, pigments, and the like.

In still another embodiment of the method of the present invention, one or more glass and/or glass ceramic frits are milled separately. The flits are then mixed and an opacifying agent may be added thereto. The mixture is then milled to the desired particle sizes. Optionally, pigments or other additives may be added to the mixture.

Pigments which may be added to the mixtures herein include but are not limited to vanadates, manganates, chromates, other transition metal oxides and the like that are conventionally used in the dental field to obtain various shades of porcelain to simulate actual shades of natural dentition. If desired, fluorescing agents such as cerium oxide, terbium oxide, yttrium oxide, and the like or other conventional additives can also be incorporated into the porcelain to simulate natural dentition.

The porcelain powder may then be wetted with a liquid vehicle to form a paste for application to a core or other material. The liquid vehicle may include but is not limited to water such as deionized water and demineralized water, organic solvents such as butylene glycol, diethylene glycol, propylene glycol, glycerin and other liquid carriers that are inert to the reaction between the porcelain and the core framework. Other solid or liquid components can be added to provide certain properties, such as dimethyl dichlorosilane, available from Union Carbide under the name Aerosil R972, to prevent separation of the powder from the liquid. Suitable surfactants such as polyalkylene oxide, available from OSi Specialties under the name Silwet L-77, and sodium dioctyl sulfosuccinate, available from Cyanamid under the name Aerosol OT-70PG, can be added to enhance wetting. One preferred combination of liquid additives includes 40 to 65 parts 1,4 butanediol 40 to 50 parts glycerin, 0 to 4 parts sodium dioctyl sulfosuccinate, and 0 to 1 part polyalkylene oxide. To the liquid mixture is added 0 to 4 parts dimethyl dichloro-silane to prevent powder separation. The powder to liquid ratio can vary between 50/50 to 80/20. A preferred mixing ratio is 67 parts powder to 33 parts liquid. Upon heating to fusion temperatures, the liquid typically evaporates and is preferably completely removed from the system. The paste may be applied to the core framework and heated to about 750° C. to 1010° C. whereat it fuses to form a dental restoration.

The following examples illustrate the practice of the invention.

EXAMPLE 1

A number of glass and glass-ceramic frits were milled separately to the desired particle size in accordance with the claimed invention as set forth above. The frits were then mixed together and the following composition was obtained:

| component | weight percent |
|---|---|
| $SiO_2$ | 65.04 |
| $Al_2O_3$ | 15.59 |
| ZnO | 0.07 |
| CaO | 0.79 |

| component | weight percent |
|---|---|
| MgO | 0.23 |
| Li$_2$O | 1.40 |
| K$_2$O | 13.39 |
| Na$_2$O | 3.07 |
| CeO$_2$ | 0.43 |

SnO$_2$, having an average particle size of less than about 2.8 microns and a maximum particle size of less than about 76 microns was added in an amount of 20.2 parts by weight to 77.9 parts by weight of the above composition to provide opacifying properties thereto. Additionally, 1.2 parts of Al$_2$O$_3$ and 0.7 parts of TiO$_2$ were added to form a white porcelain powder. The powder was then milled to the desired particle size. A liquid component comprising 52 parts 1,4 butanediol, 42.8 parts glycerin, 2 parts Aerosol OT 70PG, 0.1 parts Silwet L-77, and 3.1 parts Aerosil R972, was added to the porcelain powder in a ratio of 33 parts liquid to 67 parts powder. The paste was easily spreadable and applied to a metal framework to form an enamel layer on a crown and was air-dried for approximately 6 to 8 minutes. It was then placed in a vacuum atmosphere at approximately 1000° F. and heated at a rate of 100° F./min to 1740° F, at which point it was released from the vacuum Heating was continued to 1840° F. The porcelain was examined for surface defects such as cracking and pinholes. No defects were present.

EXAMPLE 2

The porcelain composition of Example 1 was prepared and the appropriate pigments were added to create a shaded porcelain. The shaded porcelain was mixed with a liquid component as in Example 1 using a 67/33 powder to liquid ratio and applied to a metal coping as in Example 1. The porcelain paste was air dried for approximately 6 to 8 minutes. It was then placed in a vacuum atmosphere at approximately 1000° F. and heated at a rate of 100° F./min to 1740° F. at which point it was released from the vacuum. Heating was continued to 1840° F. The porcelain was examined for surface defects such as cracking and pinholes. No defects were present.

EXAMPLE 3

A number of glass and glass-ceramic frits were milled separately and then blended to provide the following composition:

| component | weight percent |
|---|---|
| SiO$_2$ | 65.17 |
| Al$_2$O$_3$ | 16.24 |
| ZnO | 0.06 |
| CaO | 0.90 |
| MgO | 0.21 |
| Li$_2$O | 1.43 |
| K$_2$O | 12.00 |
| Na$_2$O | 3.46 |
| CeO$_2$ | 0.39 |
| B$_2$O$_3$ | 0.08 |
| BaO | 0.06 |

ZrO$_2$, having an average particle size of about 0.2 to 0.4 microns, was added in an amount of 20 parts by weight to 78.8 parts by weight of the above composition to provide opacifying properties thereto. Additionally, 1.2 parts of Al$_2$O$_3$ was added to the mixture. The appropriate pigments were added to create a shaded porcelain. A liquid component comprising 37.1 parts diethylene glycol, 55.6 parts glycerin, 2.4 parts Aerosol OT 70PG, and 4.85 parts Aerosil R972 was added to the shaded porcelain powder in a powder/liquid ratio of 71/29. The paste was applied to an alloy coping and was air-dried for approximately 6 to 8 months. It was then placed in a vacuum atmosphere at approximately 1000° F. and heated at a rate of 100° F./min to 1740° F. at which point it was released from vacuum. Heating was continued to 1840° F. The porcelain was examined for surface defects such as cracking and pinholes. No defects were present.

As will be appreciated, the present invention provides a porcelain composition having optimum particle distribution that yields good processing properties, particularly for use in the fabrication of dental restorations.

While various descriptions of the present invention are described above, it should be understood that the various features can be used singly or in any combination thereof Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A porcelain composition comprising:

particulate comprising one or more particulate components selected from the group consisting of glass powder and glass-ceramic powder and mixtures thereof;

wherein the particulate has a $d_{50}$ of from about 3 to about 6 microns; a $d_{90}$ of from about 8 to about 16 microns; and wherein about 1.0 to about 4.0% by volume of the particulate has a particle size greater than or equal to about 20 microns.

2. The composition of claim 1 wherein the particulate further comprises a $d_{10}$ of from about 1.1 to about 1.8 microns.

3. The composition of claim 1 wherein the maximum particle size of the particulate is less than about 60 microns.

4. The composition of claim 1 wherein the particulate further comprises at least one of an opacifying agent, a pigmenting agent and a fluorescing agent.

5. The composition of claim 1 wherein the particulate has a mean particle size in the range of about 3.0 to about 7.5 microns.

6. The composition of claim 1 comprising:

from about 40% to about 85% SiO$_2$;

from about 2% to about 18% Al$_2$O$_3$; and from about 2% to about 23% of a flux;

wherein the flux component is selected from the group consisting of K$_2$O, Na$_2$O, Li$_2$O, CaO, P$_2$O$_5$, F, BaO, B$_2$O$_3$ and mixtures thereof.

7. The composition of claim 6 further comprising:

up to about 6% MeO;

up to about 25% of an opacifier; and up to about 30% of a pigment;

wherein Me is a component selected from the group consisting of Zn, Mg, and mixtures thereof; the opacifier is a component selected from the group consisting of $TiO_2$, $ZrO_2$, $CeO_2$, $Y_2O_3$, $ZrO_2.SiO_2$, $SnO_2$ and mixtures thereof; and the pigment is a component selected from the group consisting of transition metal oxides and mixtures thereof.

8. The composition of claim 7 wherein the transition metal oxides comprise vanadates, manganates, and chromates.

9. The composition of claim 1 having a fired coefficient of thermal expansion in the range of about 2 to about $18\times10^{-6}/°C$. measured from room temperature to 450° C.

10. The composition of claim 1 having a fusion temperature of from about 750° to about 1010° C.

11. A dental restoration comprising a metal alloy or ceramic framework and at least one coating comprising the porcelain composition of claim 1 fused thereon.

12. A dental restoration comprising a metal alloy or ceramic framework and at least one coating comprising the porcelain composition of claim 6 fused thereon.

13. A porcelain composition comprising:
   particulate comprising one or more particulate components selected from the group consisting of glass powder and glass-ceramic powder and mixtures thereof;
   wherein particulate has a $d_{50}$ of from about 3.5 to about 5.5 microns; a $d_{90}$ of from about 10 to about 14.5 microns; and
   wherein about 1.0 to about 4.0%/o by volume of the particulate has a particle size greater than or equal to about 20 microns.

14. The composition of claim 13 wherein the particulate further comprises a $d_{10}$ of from about 1.15 to about 1.65 microns.

15. The composition of claim 13 wherein the maximum particle size of the particulate is less than about 50 microns.

16. The composition of claim 13 wherein the particulate comprises a mean particle size in the range of about 3.5 to about 6.75 microns.

17. The composition of claim 13 wherein the particulate further comprises at least one of an opacifying agent, a pigmenting agent and a fluorescing agent.

18. An inlay, onlay or veneer comprising the porcelain composition of claim 1.

19. An inlay, onlay or veneer comprising the porcelain composition of claim 6.

20. An inlay, onlay or veneer comprising the porcelain composition of claim 13.

21. A porcelain paste composition comprising:
   particulate comprising one or more particulate components selected from the group of glass powder and glass-ceramic powder and mixtures thereof; and
   a liquid vehicle;
   wherein the particulate has a $d_{50}$ of from about 3 to about 6 microns; a $d_{90}$ of from about 8 to about 16 microns; and
   wherein about 1.0 to about 4.0% by volume of the particulate has a particle size greater than or equal to about 20 microns.

22. The composition of claim 21 wherein the particulate further comprise a $d_{10}$ of from about 1.1 to about 1.8 microns.

23. The composition of claim 21 wherein the maximum particle size of the particulate is less than about 60 microns.

24. The composition of claim 21 wherein the mean particle size is in the range of about 3.0 to about 7.5 microns.

25. The composition of claim 21 wherein the particulate further comprises at least one of an opacifying agent, a pigmenting agent and a fluorescing agent.

26. The composition of claim 21 wherein the liquid vehicle is a component selected from the group consisting of deionized water, demineralized water, butylene glycol, diethylene glycol, propylene glycol, glycerin and mixtures thereof.

27. The composition of claim 21 further comprising a surfactant.

28. The composition of claim 27 wherein the surfactant is selected from the group consisting of polyalkylene oxide and sodium dioctyl sulfosuccinate.

29. The composition of claim 21 further comprising dimethyl dichloro-silane.

30. A method of making a dental restoration comprising:
   applying a porcelain layer onto a core component selected from the group consisting of a metal and ceramic framework; and
   firing at a temperature for a period of time to form a veneer;
   wherein the porcelain layer comprises the composition of claim 1.

31. The method of claim 30 wherein the core component is a ceramic framework and the firing temperature is in the range of about 750° C. to about 1010° C.

32. The method of claim 30 wherein the core component is a metal framework and the firing temperature is in the range of about 750° C. to about 1010° C.

33. A method of making a porcelain composition comprising:
   mixing two or more frits selected from the group of glass and glass-ceramic frits to form a particulate mixture;
   milling the particulate mixture to particle sizes having a $d_{10}$ of from about 1.1 and about 1.8 microns; a $d_{50}$ of from about 3 to about 6 microns; and a $d_{90}$ of from about 8 to about 16 microns; and
   wherein about 1.0 to about 4.0% by volume of the particulate has a particle size greater than or equal to about 20 microns.

34. The method of claim 33 wherein the particulate has a maximum particle size of less than about 60 microns.

35. The method of claim 33 further comprising adding at least one of an opacifying agent, a pigmenting agent and a fluorescing agent to the particulate mixture.

36. The method of claim 33 wherein the particulate is milled to a mean particle size of from about 3.0 to about 7.5 microns.

37. A method of making a porcelain composition comprising:
   selecting a frit from the group of glass and glass-ceramic frits;
   milling the frit to particle sizes to form a particulate mixture wherein the particulate mixture has a $d_{10}$ of from about 1.1 to about 1.8 microns; a $d_{50}$ of from about 3 to about 6 microns; and a $d_{90}$ of from about 8 to about 16 microns; and
   wherein about 1.0 to about 4.0% by volume of the particulate has a particle size greater than or equal to about 20 microns.

38. The method of claim 37 wherein the particulate is milled to a maximum particle size of less than about 60 microns.

39. The method of claim 37 further including adding at least one of an opacifying agent, a pigmenting agent and a fluorescing agent to the particulate mixture.

40. The method of claim 37 wherein the milled has a mean particle size of from about 3.0 to about 7.5 microns.

41. A method of making a porcelain composition comprising:

milling separately two or more frits, selected from the group of glass and glass-ceramic frits, to a particulate wherein the particulate has a $d_{50}$ of from about 3 to about 6 microns; a $d_{90}$ of from about 8 to about 16 microns; and wherein about 1.0 to about 4.0% by volume of the particulate has a particle size greater than or equal to about 20 microns; and mixing the two or more milled frits together to form a particulate mixture.

42. The method of claim 41 wherein the flits are milled to a maximum particle size of less than about 60 microns.

43. The method of claim 41 further including adding at least one of an opacifying agent, a pigmenting agent and a fluorescing agent to the particulate mixture.

44. The method of claim 43 wherein the frits are milled to a particulate having a mean particle size in the range of from about 3.0 to about 6.5 microns.

45. A method of making a porcelain composition comprising:

milling separately two or more flits, selected from the group of glass and glass-ceramic frits;

mixing the frits to form a particulate powder mixture;

adding an opacifying agent to the particulate powder mixture to form a particulate powder-opacifying mixture; and milling the particulate powder-opacilying mixture to particle sizes wherein the particulate powder-opacifying mixture has a $d_{50}$ of from about 3 to about 6 microns; a $d_{90}$ of from about 8 to about 16 microns; and wherein about 1.0 to about 4.0% by volume of the particulate has a particle size greater than or equal to about 20 microns.

46. The method of claim 45 wherein the particulate powder-opacifier mixture is milled to a maximum particle size of less than about 60 microns.

47. The method of claim 45 wherein the opacifying agent is selected from the group consisting of $TiO_2$, $ZrO_2$, $CeO_2$, $Y_2O_3$, $ZrO_2.SiO_2$, $SnO_2$ and mixtures thereof.

48. The method of claim 45 wherein the particulate powder-opacifing mixture has a mean particle size of from about 3.0 to about 7.5 microns.

49. A method of making a porcelain composition comprising:

milling separately two or more frits, selected from the group of glass and glass-ceramic frits;

mixing the two or more flits to obtain a particulate mixture;

wherein the particulate mixture comprises a particulate having a $d_{50}$ of from about 3 to about 6 microns; a $d_{90}$ of from about 8 to about 16 microns; and wherein about 1.0 to about 4.0% by volume of the particulate has a particle size greater than or equal to about 20 microns.

50. The method of claim 49 wherein the particulate comprises a maximum particle size of less than about 60 microns.

51. The method of claim 49 further including adding at least one of an opacifying agent, a pigmenting agent and a fluorescing agent to the particulate mixture.

52. The method of claim 49 wherein the mixture has a mean particle size in the range of from about 3.0 to about 7.5 microns.

* * * * *